US006692757B1

(12) United States Patent
Day et al.

(10) Patent No.: US 6,692,757 B1
(45) Date of Patent: Feb. 17, 2004

(54) MULTI-COMPONENT, SAFE BIOCIDAL COMPLEX

(75) Inventors: Donal F. Day, Baton Rouge, LA (US); Charlie M. Ott, Seabrook, TX (US); John A. Mayo, Metairie, LA (US); Duwoon Kim, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/382,286

(22) Filed: Aug. 24, 1999

(51) Int. Cl.$^7$ ................................................. A01N 25/32
(52) U.S. Cl. ........................ 424/406; 424/405; 424/613; 424/616; 514/557; 514/635; 514/709; 514/730; 514/731; 514/738
(58) Field of Search ................................. 424/405, 613, 424/615, 617, 406, 616; 514/557, 730, 731, 635, 738, 709

(56) References Cited

U.S. PATENT DOCUMENTS

| | | | | |
|---|---|---|---|---|
| 4,119,535 A | * | 10/1978 | White et al. | .................. 210/62 |
| 5,320,805 A | | 6/1994 | Kramer et al. | ................. 422/28 |
| 5,344,652 A | | 9/1994 | Hall, II et al. | .............. 424/405 |
| 5,407,656 A | * | 4/1995 | Roozdar | |
| 5,489,434 A | | 2/1996 | Oakes et al. | ................. 424/405 |
| 5,725,678 A | | 3/1998 | Cannon et al. | ................. 134/1 |
| 5,731,275 A | | 3/1998 | Prevost et al. | .............. 510/161 |
| 5,759,970 A | | 6/1998 | Prevost et al. | .............. 510/161 |
| 5,880,076 A | * | 3/1999 | Vermeer | ...................... 510/123 |

FOREIGN PATENT DOCUMENTS

| FR | 2 578988 | * | 9/1986 |
|---|---|---|---|
| GB | 2257630 | * | 1/1993 |

OTHER PUBLICATIONS

Abel et al., "Studies on Dental Aerobiology, IV. Bacterial Contamination of Water Delivered by Dental Units," J. Dental Res., vol. 50, pp. 1567–1569 (1971).

Heckmann, R.A., "Quality control and evaluation of milking machines liners (inflations) and milk tubes using scanning electron microscopy and x–ray microanalysis," USA Microscopy and Analysis, Nov. 1997, pp. 19–21 (1997).

Kim, D.W. et al., "Effect of a novel biocide as an alternative to chlorine treatment for *Salmonella typhimurium* and *Escherichia coli*," 99$^{th}$ American Society of Microbiology General Meeting, Jun. 1, 1999, Chicago, Illinois, Abstract No. P–57 (1999).

(List continued on next page.)

*Primary Examiner*—Neil S. Levy
(74) *Attorney, Agent, or Firm*—Bonnie J. Davis; John H. Runnels

(57) ABSTRACT

A novel composition has been discovered for decontaminating biofilm-contaminated surfaces (the "Biocidal Complex"). The novel composition both kills bacteria and destroys at least a part of the biofilm. The composition comprises an effective amount of a free-radical generating compound (e.g., hydrogen peroxide), a disinfectant from the "GRAS" list of food-safe compounds (e.g., thymol), and an acid sulfate such as sodium bisulfate ($NaHSO_4$) to acidify the solution and help catalyze free radical formation. A preferred method of using this invention employs a multi-component approach that permits long-term storage of the components in a stable, concentrated form. Immediately before use, the components are mixed and then applied to the biofilm-contaminated surface. A separate metal catalyst for the generation of free-radicals may be added to increase the production of free radicals in the Biocidal Complex. This invention offers a safe, effective, and easy method for disinfecting and decontaminating biofilm-contaminated surfaces, including dental unit water lines.

27 Claims, 8 Drawing Sheets

OTHER PUBLICATIONS

Mayo, J.A. et al., "Bacterial Biofilm: A Source of Contamination in Dental Air–Water Syringes," Clinical Preventive Dentistry, vol. 12 (3), pp. 13–20 (1990).

Mayo, J.A. et al., "Effect of in–line bacteriological filters on numbers of heterotrophic bacteria in water emitted from non–autoclavable dental air–water syringes," American Journal of Dentistry, pp. 1–24, accepted for publication (1999).

Miller, C.H., "Microbes in Dental Unit Water," CDA Journal, vol. 24, pp. 47–52 (1996).

Murdoch–Kinch, C.A. et al., "Comparison of Dental Water Quality Management Procedures," JADA, vol. 128, pp. 1235–1243 (1997).

Peters, E. et al., "Dental Unit Water Contamination," Journal of the Canadian Dental Association, vol. 62, pp. 492–495 (1996).

Sapers, G.M. et al. "Hydrogen peroxide disinfection of minimally processed fruits and vegetables," Food Technology, vol. 52, No. 2, pp. 48–50, 1998).

The Merck Index, Twelfth Edition (1996), Monograph 8729, p. 1472.

Wood, P. et al., "Surface–catalysed disinfection of thick *Pseudomonas aeruginosa* biofilms," Journal of Applied Microbiology, vol. 84, pp. 1092–1098 (1998).

* cited by examiner

MULTI-COMPONENT, SAFE BIOCIDAL COMPLEX

The development of this invention was partially funded by the Government under grant no. HBR NGT 9-10 from the National Aeronautic and Space Administration. The Government has certain rights in this invention.

This invention pertains to a composition for decontaminating biofilm-contaminated surfaces, particularly to a composition that both destroys the biofilm and kills bacteria.

Biofilms are microbial populations adherent to surfaces that are in constant or intermittent contact with water. Biofilms are typically composed of bacteria and other microorganisms in a biopolymer matrix, both produced by the microbial population and derived from the surrounding environment. A biofilm environment enhances microbial growth on surfaces in various ways. It allows a microbe to be retained on a surface instead of being swept away by a fluid, permits better nutrient assimilation, and provides the bacteria some degree of protection from phagocytes, antibiotics, immunoglobulins, surfactants and disinfectants. J. A. Mayo et al., "Bacterial Biofilm: A Source of Contamination in Dental Air-Water Syringes," Clinical Preventive Dentistry, vol. 12 (3), pp. 13–20 (1990).

Biofilms have deleterious effects on industrial and biological systems. Biofilms can cause corrosion, plugging of filters, fouling of heat exchangers, and reduction of flow through pipelines. Unwanted biofilms can accumulate in the distribution pipes of city water systems and in milk transfer pipes of the dairy industry. See, R. A. Heckmann, "Quality control and evaluation of milking machines liners (inflations) and milk tubes using scanning electron microscopy and x-ray microanalysis," USA Microscopy and Analysis, November 1997, pp. 19–21(1997); and Mayo et al., 1990. Conditions such as dental plaque and diseases such as dental caries and endocarditis involve the accumulation of biofilms within the body.

Materials contaminated with biofilm bacteria are particularly difficult to sterilize or disinfect. The shape, size, and location of equipment often makes heat sterilization difficult or, in some cases, impossible. Moreover, many materials are not heat stable.

One area of particular concern is contamination of water lines in dental clinics. The dental unit water may be contaminated by the release of microorganisms from biofilms located on the lumen surfaces of the water lines. Dental unit water can harbor high concentrations of bacterial contaminants, with values ranging from 20,000 to 500,000 colony-forming units (cfu) of bacteria per milliliter (ml) of water. For comparison, faucet water from the same sites showed bacterial counts of 0 to 15 cfu/ml. Mayo et al., 1990. Organisms found in dental unit water include opportunistic pathogens that may cause harmful infections in immunocompromised patients. Additionally, the bleeding that commonly occurs during dental procedures exposes both healthy and immunocompromised patients to the possibility of infections.

Dental unit biofilms have been found to contain various species of Legionella bacteria, including the causative agent of Legionnaires' disease, *Legionella pneumophila*. Biofilms in water lines may also harbor bacteria known to be involved in causing dental caries or periodontal diseases (Bacteroides, Fusobacterium, Lactobacillus, Peptostreptococcus, Streptococcus). C. H. Miller, "Microbes in Dental Unit Water," CDA Journal, vol. 24, pp. 47–52 (1996).

Mechanical and chemical methods aimed at reducing bacterial contamination of water lines have been unable to eliminate the problem of rapid reinfection of water lines. If a biofilm is not completely removed, bacteria remaining in the biofilm rapidly proliferate and reinfect the water lines. Flushing of high-speed handpieces and dental unit water lines as recommended by the Centers for Disease Control results in only a transient reduction in the microbial count of the effluent water. This procedure does not dislodge the biofilm on the lumen surface in the water lines, and therefore does not prevent recontamination of the water by bacteria remaining in the biofilm. C. H. Miller, CDA Journal, vol. 24, pp 47–52, 1996. In line filters can remove or reduce the bacteria found in dental unit water, but cannot directly reduce biofilms in the water lines. C. A. Murdoch-Kinch et al., "Comparison of Dental Water Quality Management Procedures," JADA, vol. 128, pp. 1235–1243 (1997). Other suggested treatments, including drying water lines or using steam to purge lines, are either not practical in dental water systems or not often used in practice because of the time and training necessary.

Methods using chemical disinfection to kill biofilm bacteria in dental unit water lines include using alcohol (70% v/v), povidone-iodine (10% solution), acids (e.g., a mixture of mandelic and lactic acids), sodium hypochlorite, and peroxyacids. See Abel et al., "Studies on Dental Aerobiology, IV. Bacterial Contamination of Water Delivered by Dental Units," J. Dental Res., Vol. 50, pp. 1567–1569 (1971); and E. Peters et al., "Dental Unit Water Contamination," Journal of the Canadian Dental Association, vol. 62, pp. 492–495 (1996). Commercially available antiseptic compositions include chlorhexidine, BIOVAC™ (chlorhexidine, EDTA, proteolytic enzymes, and a dispersing agent), EFFERDENT™ (potassium monopersulphate, sodium borate, sodium lauryl persulfate, sodium bicarbonate, magnesium stearate, and simethicone), POLYDENT™ (potassium monopersulphate, tetrasodium pyrophosphate, sodium bicarbonate, and sodium borate), STERISOLT™ (chlorhexidine, glycerol, 38-F, and alcohol), THERASOL™ (C-31G, sodium fluoride, glycerine, and alcohol), and PATHEX™ (phenolic).

Another approach to killing biofilm bacteria is to damage bacterial proteins with denaturing agents such as glutaraldehyde or sodium lauryl sulfate (which has both denaturing and detergent properties). However, the biopolymer matrix surrounding biofilm bacteria reduces the effectiveness of many of these biocidal treatments by blocking access to the target organisms. As a result, many of these treatments cause only a temporary reduction in bacterial numbers until the remaining bacteria proliferate and reinfect both the surface and the liquids flowing over the biofilm-contaminated surface.

Peroxides have been used as a source of highly reactive free radicals to attack and disinfect biofilm-contaminated surfaces. Hydrogen peroxide is classified as "generally recognized as safe" (GRAS) and is used in a 5% solution to wash fruits and vegetables. See G. M. Sapers et al. "Hydrogen peroxide disinfection of minimally processed fruits and vegetables," Food Technology, vol. 52, no. 2, pp 48–50, 1998). The anti-biofilm biocidal action of peroxides and persulfate is significantly enhanced by incorporation of transition metal catalysts into the surfaces to be cleaned. See P. Wood et al., "Surface-catalysed disinfection of thick *Pseudomonas aeruginosa* biofilms," Journal of Applied Microbiology, vol. 84, pp. 1092–1098 (1998).

Although some treatments appear to effectively kill biofilm bacteria, they do not dislodge the biofilm matrix from surfaces. Alternately, treatments that attack the matrix do not necessarily kill the biofilm bacteria. Detergents (e.g., Tween 80) can be used to dislodge biofilm from small diameter dental unit waterlines, but detergent alone does not effectively destroy the microorganisms present in the biofilm.

U.S. Pat. No. 5,320,805 discloses a disinfectant comprising alkaline water-soluble salts having hydrogen peroxide crystallization (e.g., sodium carbonate-hydrogen peroxide of crystallization) and a positively charged phase transfer agent (e.g., phosphonium salt, sulfonium salt, or quaternary ammonium salt), which form a water- and lipid-soluble phase-transfer ion pair that can pass between aqueous and lipid phases.

U.S. Pat. No. 5,725,678 discloses cleaning organic residues from surfaces using hydrogen peroxide, where the effectiveness of the process is enhanced by iron or other catalysts or enhancers.

U.S. Pat. No. 5,344,652 discloses an anticorrosive microbiocidal solution that combines a mixture of acetic acid, hydrogen peroxide, peracetic acid, and water with a wetting agent.

U.S. Pat. Nos. 5,731,275 and 5,759,970 disclose a composition to clean and disinfect biofilm-contaminated surfaces containing all of the following: a detergent for reducing the surface tension of the biofilm, a denaturing agent for affecting the integrity of proteins and mucopolysaccharides of both the bacteria and the extracellular matrix, and a wide-spectrum disinfectant.

U.S. Pat. No. 5,489,434 discloses an antimicrobial composition comprising various combinations of a $C_5$ peroxyacid, with a $C_1$–$C_4$ peroxyacid, or a $C_6$–$C_{18}$ peroxyacid.

The prior treatments suffer several disadvantages. Treatments using detergents, denaturants, and strong disinfectants often require extensive rinsing of the treated water lines or other surfaces before they are safe for human use again. Use of volatile compounds with strong odors (e.g., peracetic acid) can be disagreeable or even harmful; use of sodium hypochlorite (bleach; NaOCl) may cause corrosion of in-line metal valves; and use of steam or drying may cause long-term damage to the surfaces being decontaminated.

There remains a need for a safe composition that is effective for decontaminating water lines and other surfaces by killing bacteria and destroying at least a part of the biofilm.

We have discovered a novel composition for decontaminating biofilm-contaminated surfaces (the "Biocidal Complex"). The novel composition both kills bacteria and destroys at least a part of the biofilm. The composition comprises an effective amount of a free-radical-generating compound (e.g., hydrogen peroxide), a disinfectant from the "GRAS" list of food-safe compounds (e.g., thymol), and an acid sulfate such as sodium bisulfate ($NaHSO_4$) to acidify the solution and help catalyze free radical formation. A preferred method of using this invention employs a multi-component approach that permits long-term storage of the components in a stable, concentrated form. Immediately before use, the components are mixed and then applied to the biofilm-contaminated surface. A separate metal catalyst for the generation of free-radicals may be added to increase the production of free radicals in the Biocidal Complex. This invention offers a safe, effective, and easy method for disinfecting and decontaminating biofilm-contaminated surfaces, including water lines in dental units.

Figure 1:
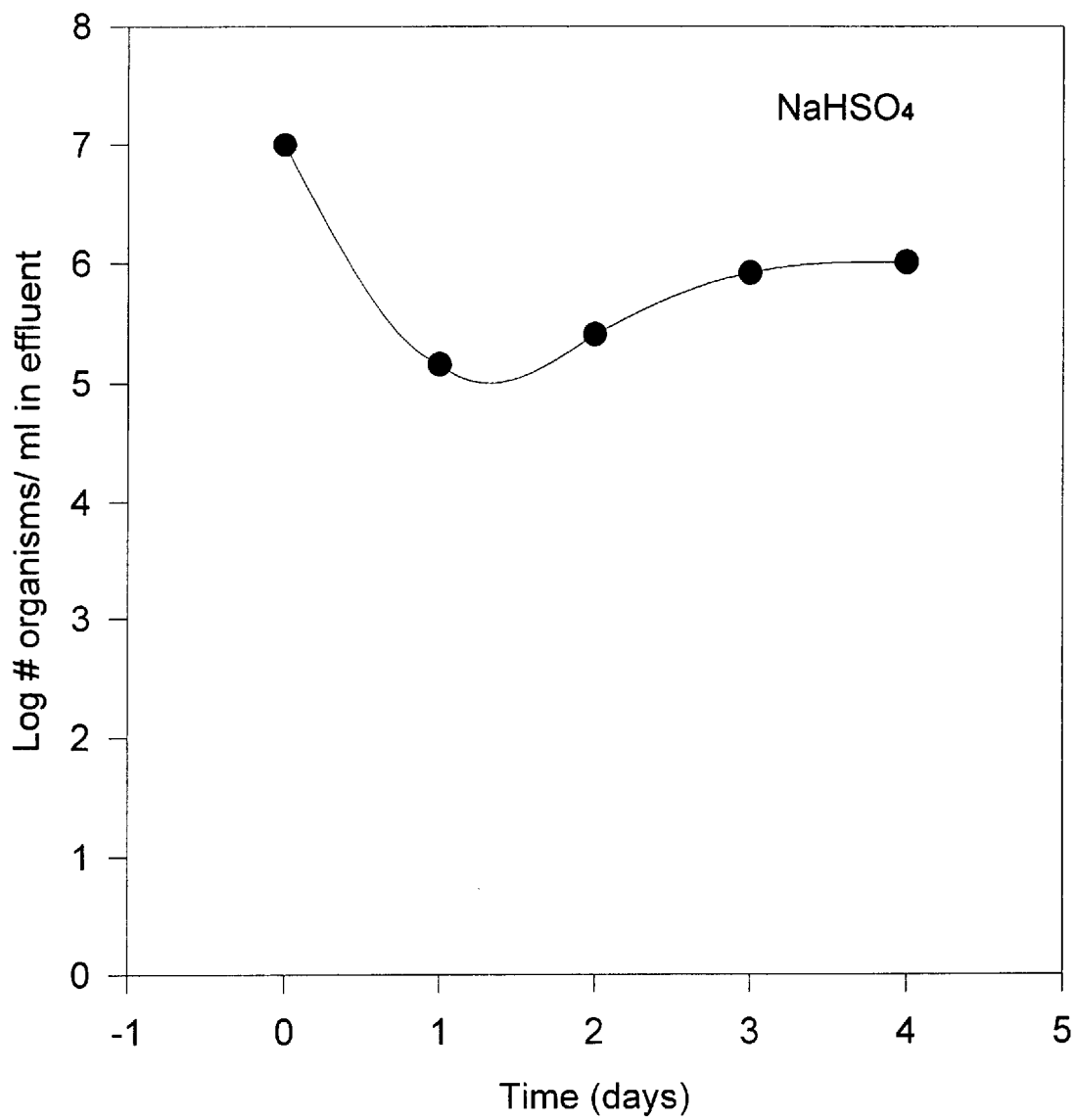
FIG. 1 illustrates the change in bacterial concentration in the effluent of biofilm-contaminated glass beads after treating with $NaHSO_4$ alone.

The present invention provides a method for disinfecting contaminated surfaces such as dental unit water lines by exposing these surfaces to an active Biocidal Complex capable of both destroying at least part of the biofilm and killing the bacteria. A preferred embodiment used a two-component system in which one component comprised hydrogen peroxide in either solid or liquid form, while the second component comprised a solution of sodium bisulfate and thymol. These components were mixed and passed across a metallic iron catalyst, which increased the rate of peroxide breakdown and the generation of the active Biocidal Complex. The active complex was then injected into dental unit water lines. The best results were achieved when Biocidal Complex was injected immediately after activation, but the complex remained effective for about 12 hours after activation. Although the bulk of biofilm destruction probably occurred within the first hour of treatment, the active complex could be left in the lines for convenience until the next desired use of the unit. Prior to use, the lines were flushed with water for a minimum of two minutes, as required by the Centers for Disease Control.

The Biocidal Complex may be injected into drained water lines, or a suitably concentrated composition may be added to water remaining in the lines to bring the proportions of the active ingredients to an effective final concentration.

Other contaminated surfaces were disinfected by spreading Biocidal Complex over the surfaces for a suitable treatment time. Examples include various animate and inanimate surfaces, especially those associated with food processing.

Without wishing to be bound by this theory, it is believed that the effectiveness of this composition is due to a synergistic interaction between the individual components. The mechanism of action is believed to be as follows: (1) Free radicals are generated by catalytic action. For example, active oxygen species are generated from the breakdown of hydrogen peroxide, a process accelerated by a metal catalyst such as metallic iron or by an acid sulfate such as $NaHSO_4$. (2) These free radicals, in the presence of $NaHSO_4$, attack and degrade the polymers of the biofilm matrix and may also attack and weaken bacterial cell walls and membranes. (3) The degradation of the biofilm matrix gives the biocidal compound access to the biofilm bacteria. (4) Extensive killing of the bacteria residing in the biofilm means that the surface will not be rapidly recontaminated by proliferation of bacteria persisting in the biofilm. Rinsing the surface after treatment both removes the residual ingredients and dislodges the biofilm and bacteria that have been destroyed by this treatment.

The ingredients of this composition are safe to use on surfaces that contact fluids or other materials consumed by humans. Hydrogen peroxide is on the "GRAS" list. Other peroxide salts such as mannitol peroxide are considered safe if the complexing agent (e.g., the common sugar mannitol) is considered safe. Sodium bisulfate ($NaHSO_4$), used in small amounts, has not been reported to pose a specific health risk beyond the risks inherent in handling any dilute acid solution. (The Merck Index, Eleventh Edition (1989), Monograph 8531, page 1357) The disinfectant is chosen from the "GRAS" list of compounds recognized as safe for human use, for example, thymol or chlorhexidine. When a free metal catalyst is used, it will usually be retained in the container in which the ingredients were mixed. Alternatively, the metal catalyst can be a component of the surface being disinfected (e.g., a copper surface used in food preparation). Safety is further enhanced by thoroughly rinsing the treated surfaces, as required by relevant industry standards. All components of the present composition are easily rinsed away. Thus the present invention offers a safe, effective, and easy method for disinfecting and decontaminating biofilm-contaminated surfaces.

The following elements are used to create the active Biocidal Complex: a free radical generating compound; a disinfectant; $NaHSO_4$ or an equivalent bisulfate (i.e., $KHSO_4$); and a suitable catalyst to speed the release of free radicals. Other components may be added that do not interfere with the activity of the active complex. When a surface to be decontaminated contains metals that can serve as catalysts for free radical generation, the first three components alone may be mixed and applied directly to the surface.

Free radical-generating compounds suitable for use in this composition include active oxygen species and hydroxyl radicals, including stabilized peroxides, either in liquid or solid form, e.g., hydrogen peroxide, mannitol peroxide, sodium peroxide, and barium peroxide; peroxyacids, e.g. peroxysulfuric acid; and superoxides, e.g., potassium superoxide.

Disinfectants may be selected from "GRAS" food-safe compounds, as well as other biocidal compounds that are found to be safe, including thymol, chlorhexidine, and antibiotics.

Bisulfate, such as sodium bisulfate ($NaHSO_4$) or potassium bisulfate ($KHSO_4$), is a necessary component to achieve the desired high level of biofilm decontamination.

Metal catalysts, if used, may be selected from transition metals such as iron, copper, cobalt, silver, gold, chromium, zinc, nickel, and combinations thereof.

EXAMPLE 1

Effect of Various Components of Biocidal Complex

Glass beads in a column (containing 85.3 cm² of total surface area) were washed continuously with city water for 12 hours and then the water was allowed to stand in the column for 12 hr. The beads were first contaminated with bacteria endogenous to the city water system for five days. The biofilm-contaminated beads were then treated with various combinations of the ingredients of the Biocidal Complex for four days during the 12 hours that the water was static. Microbial counts were monitored using standard water analysis procedures as described in J. A. Mayo etal., "Effect of in-line bacteriological filters on numbers of heterotrophic bacteria in water emitted from non-autoclavable dental air-water syringes," American Journal of Dentistry, accepted for publication (1999).

The following concentration of each component of Biocidal.Complex was used: hydrogen peroxide, 3% v/v; $NaHSO_4$. 0.06% w/v; and thymol, >0.1% w/v. Additionally, an iron chip was added to the Biocidal Complex. The qualitative effect of different combinations of the four components on bacteria released from the established biofilms are summarized in Table 1.

TABLE 1

Qualitative Changes in Number of Organisms Released from Established Biofilms When Treated with Various Combinations

| Components | Effect[a] |
|---|---|
| Peroxide | – |
| Iron | – |
| $NaHSO_4$ | – |
| Thymol | +/– |
| Peroxide + iron | +/– |
| Peroxide + $NaHSO_4$ | – |
| Peroxide + thymol | +/– |
| Iron | +/– |
| Iron + thymol | +/– |
| Peroxide + $NaHSO_4$ + thymol | + |
| Peroxide + iron + $NaHSO_4$ | + |
| Peroxide + iron + $NaHSO_4$ + thymol | +++ |

[a] "–" No significant reduction in number of organisms.
"+/–" A small or transient reduction in number of organisms.
"+" A significant reduction in number of organisms.
"+++" A reduction to below 10 organisms per ml effluent.

The effect of different combinations of the components of the Biocidal Complex at the same concentrations as stated above over a 4-day time course is illustrated in FIGS. 1, 2, 3, and 4. Glass beads with an established biofilm were treated, and samples collected and analyzed, as described above. FIG. 1 shows the effect of treating biofilms using only $NaHSO_4$. Although $NaHSO_4$ caused a nearly 100-fold reduction in the number of organisms in the first day, the number remained unacceptably high. The continued high numbers of organisms released from the established biofilm on glass beads indicated that $NaHSO_4$ alone did not destroy the biofilm.

Figure 2:
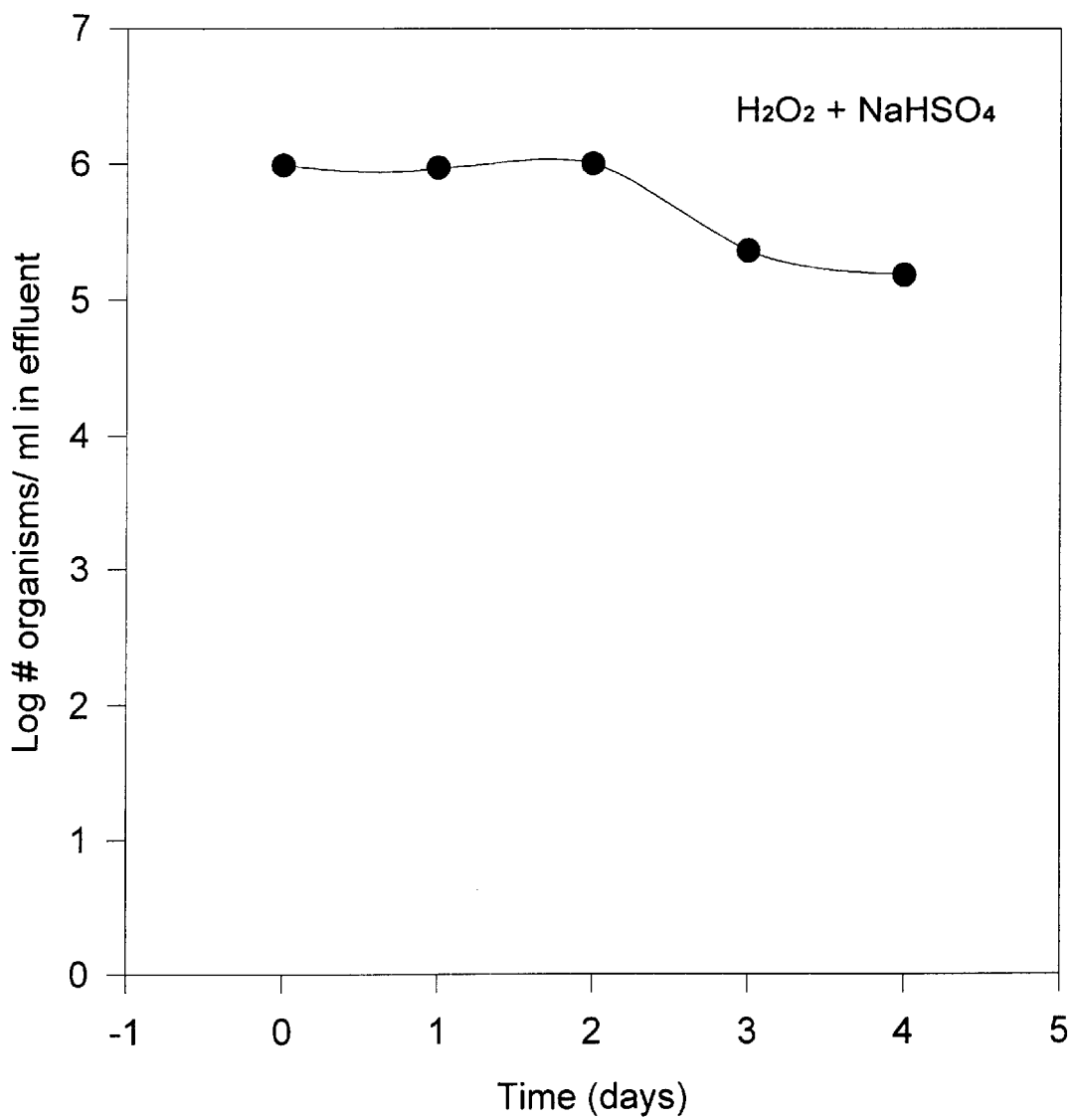
FIG. 2 illustrates the change in bacterial concentration in the effluent of biofilm-contaminated glass beads after treating with peroxide and $NaHSO_4$.

FIG. 2 shows the effect of a combination of hydrogen peroxide and $NaHSO_4$ on the release of organisms from an established biofilm. This combination caused a less than 10-fold decrease in the number of organisms released.

Figure 3:
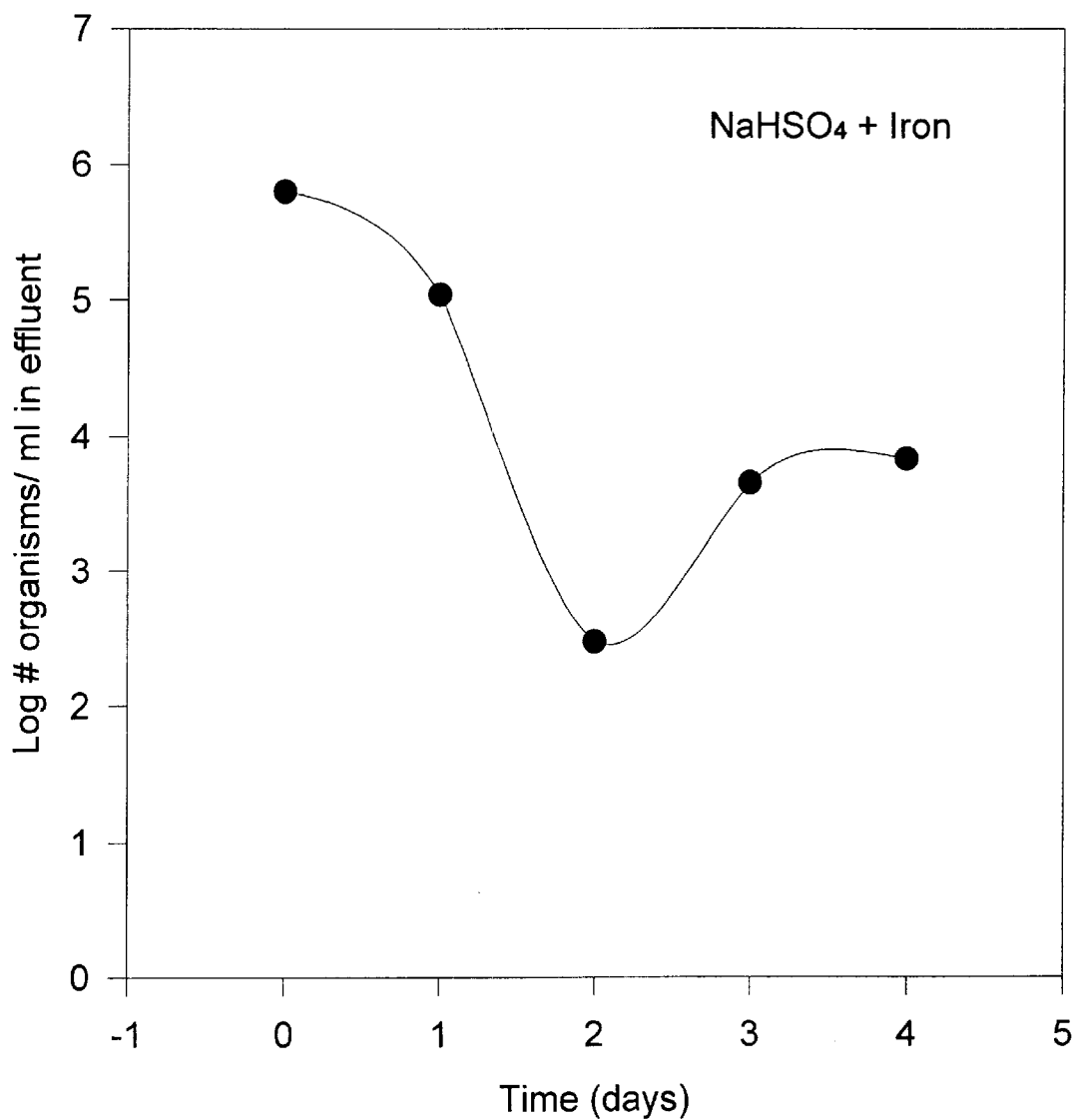
FIG. 3 illustrates the change in bacterial concentration in the effluent of biofilm-contaminated glass beads after treating with an iron chip and $NaHSO_4$.

FIG. 3 shows the effect of a combination of an iron chip and $NaHSO_4$. This combination caused a transient decrease in the concentration of organisms to less than 500 per ml on day 2, but the concentration recovered to nearly 10,000 by day 4. This transient effect and rapid recovery of organisms indicated that the combination of iron and $NaHSO_4$ did not destroy the biofilm.

Figure 4:
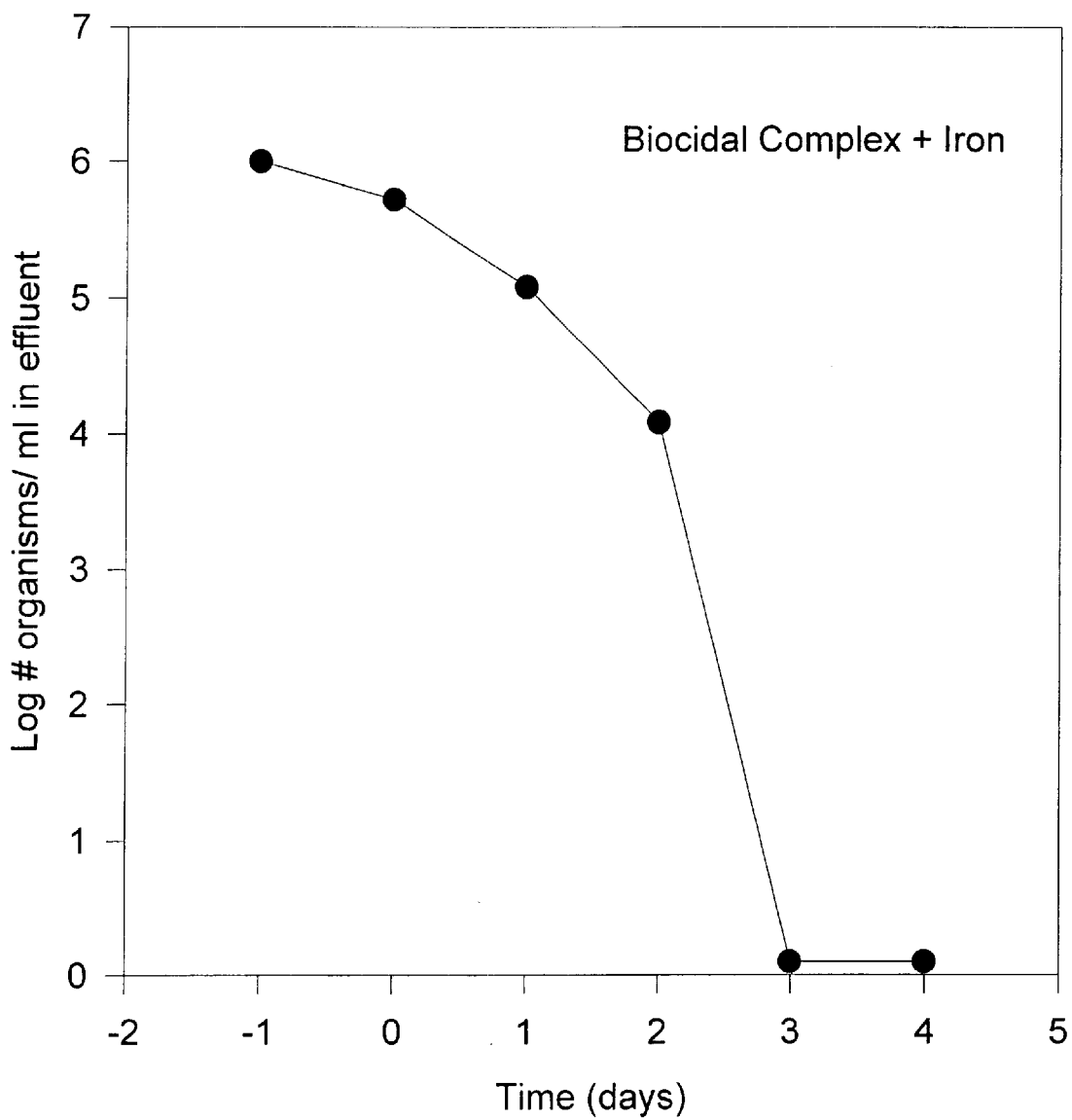
FIG. 4 illustrates the change in bacterial concentration in the effluent of biofilm-contaminated glass beads after treating with Biocidal Complex (a combination of hydrogen peroxide, $NaHSO_4$, and thymol) and an iron chip.

FIG. 4 shows the effect of Biocidal Complex (a combination of hydrogen peroxide, $NaHSO_4$ and thymol) and an iron catalyst on the number of organisms released. This combination reduced the number of organisms to nearly zero by day 3 and maintained this reduction by day 4. Only this combination appeared to destroy the biofilm such that organisms were no longer found in the effluent.

EXAMPLE 2

Use of Biocidal Complex on Small-bore TYGON® Tubing

A. Biocidal Complex was tested on small-bore TYGON® tubing that had been contaminated with bacteria from city water for five days. The active complex was formed by adding 50 ml of a solution containing 0.067% w/w thymol to a 50 ml syringe containing 5 g solid mannitol peroxide, 0.03 g $NaHSO_4$, and a chip of iron. The mixture was shaken until all solids had dissolved and was then introduced into the contaminated TYGON® tubing and allowed to stand in the tubing for 12 hr. The iron chip catalyst was retained in the syringe. City water was introduced in control (untreated) tubing and allowed to stand for 12 hr. Afterwards, the inner surfaces of both the treated and control tubing were exposed to city water for 12 hr. Samples were taken immediately prior to treatment (Day 0) and then at 24 hr intervals, i.e., following each treatment cycle. Treated tubing was subjected to a 24 hr cycle comprising 12 hr treatment with the Biocidal Complex and 12 hr standing city water. The city water in the control tubing was exchanged on a 12 hr cycle. Microbial counts were monitored using standard water analysis procedures, as described in Mayo et al., 1999, and expressed as colony-forming units per milliliter of effluent (cfu/ml). The results are summarized in Table 2.

TABLE 2

Effect of Active Biocidal Complex On Release of Organisms From Biofilm-Contaminated TYGON ® Tubing

| Time (days) | Control (cfu/ml) | Treated (cfu/ml) |
| --- | --- | --- |
| 0 | 83,000 | 1900 |
| 1 | 28,000 | 1 |
| 2 | 1,200 | 1 |
| 3 | 67,000 | 1 |
| 4 | 14,600 | 20 |
| 5 | 8,700 | 1 |

As shown in Table 2, the concentration of bacteria fluctuated widely even in the control tubing, although remaining unacceptably high. However, the active Biocidal Complex caused a reduction in microbial count to nearly zero cfu/ml after the first 24 hr cycle. This effect persisted with continued treatment. By contrast, the effluent from the untreated, control tubing continued to have a microbial count that fluctuated between a high of 83,000 cfu/ml to a low of 1,200 cfu/ml during the course of the experiment.

Figure 5:
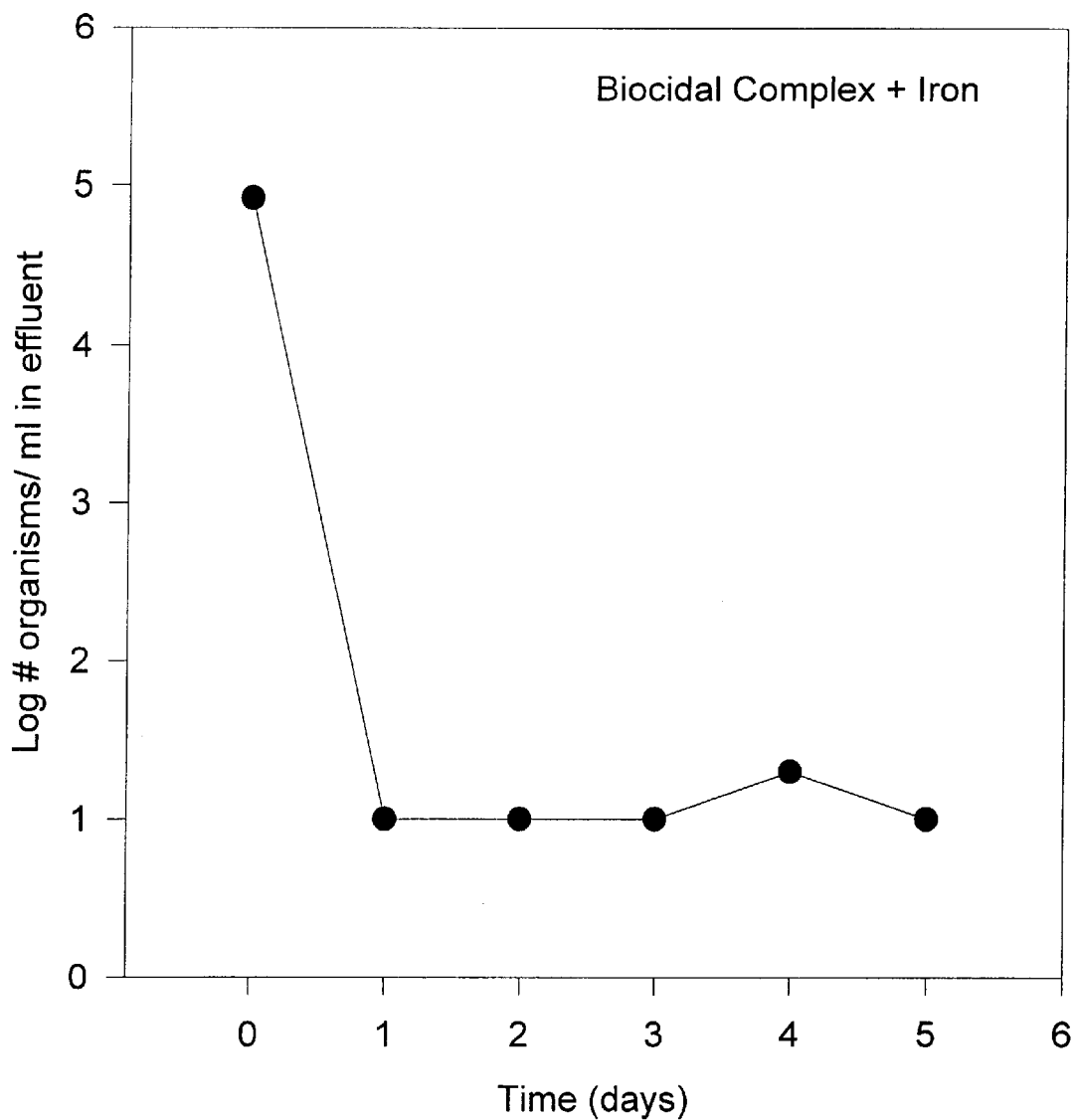
FIG. 5 illustrates the change in bacterial concentration in the effluent of biofilm-contaminated TYGON® tubing after treating with Biocidal Complex (a combination of hydrogen. peroxide, $NaHSO_4$ and thymol) and an iron chip.

B. FIG. 5 shows the effect of an active Biocidal Complex with slightly different components. TYGON® tubing was treated with Biocidal Complex (consisting of hydrogen peroxide, 3% v/v; $NaHSO_4$, 0.06% w/v; and thymol, >0.1% w/v) and an iron chip. Twelve-hour cycles of exposure to city water and treatment with Biocidal Complex were carried out as described above. The effluent from the tubing was sampled and analyzed as described above. Treatment of TYGON® tubing with this active complex resulted in a dramatic decrease in the number of organisms released from the biofilm as early as day 1, following the first cycle of treatment. The continued low numbers of organisms in the effluent indicate that Biocidal Complex effectively destroyed the biofilm.

EXAMPLE 3

Treatment of Dental Unit Water Lines

Figure 6:
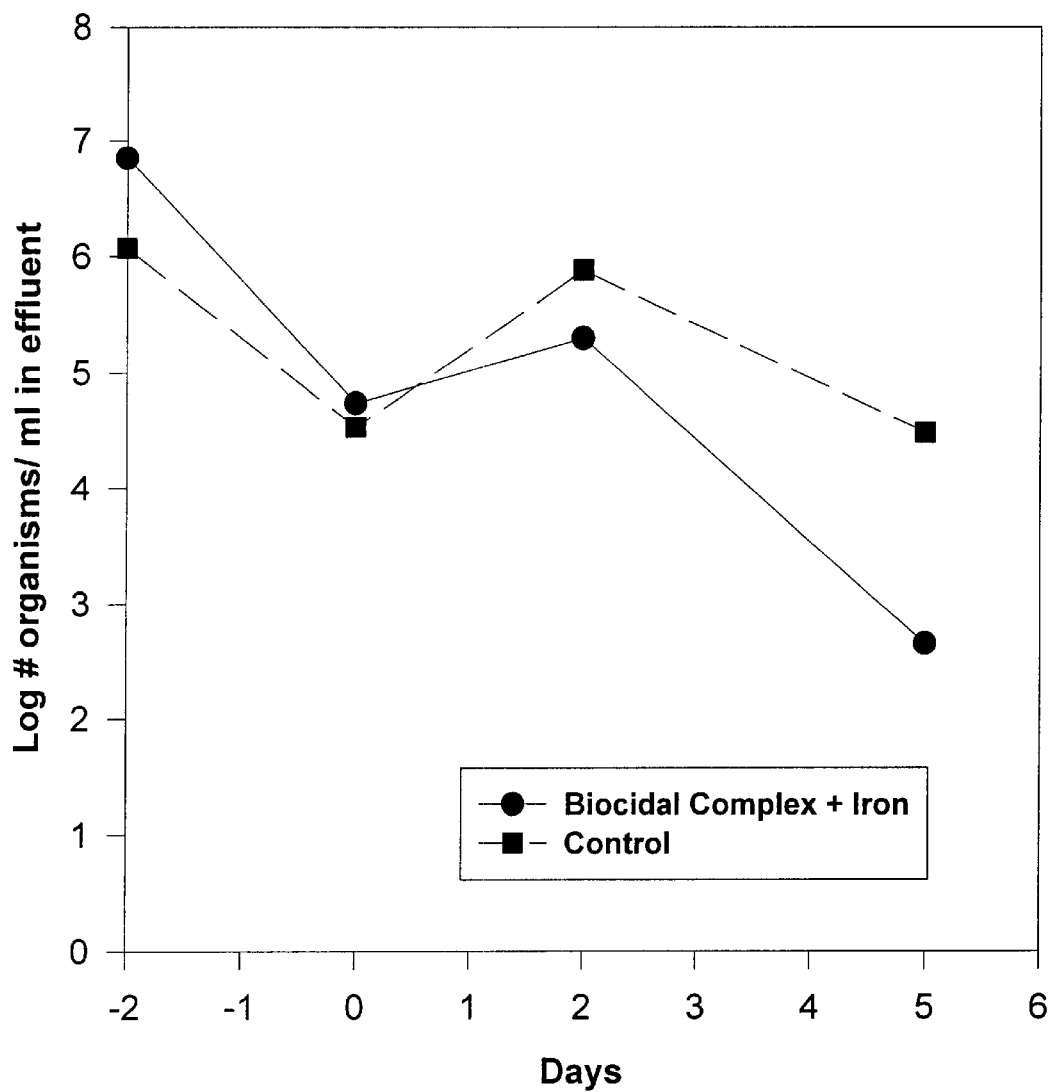
FIG. 6 illustrates the difference between the bacterial concentrations from the effluent of untreated biofilm-contaminated dental lines and the bacterial concentrations from the effluent of biofilm-contaminated water lines treated with Biocidal Complex (comprising hydrogen peroxide, $NaHSO_4$ and thymol) and an iron chip.

Water lines in a dental clinic were treated with Biocidal Complex, as described in part A of Example 2. The treated water lines were allowed to stand for 12 hours with the active Biocidal Complex when the unit was not in use. Control (untreated) lines had city water standing in the lines for the time the unit was not in use. Following the 12 hr non-use time, the lines were flushed with city water and used according to normal practice for 12 hr. This cycle was continued for 4 days. Water samples were taken at two days prior to treatment, the day of treatment, the second day of treatment, and the day following the last day of treatment. The samples were analyzed as described above in Example 2. The results are shown in FIG. 6. Day -2 corresponds to water samples taken two days prior to beginning treatment on Day 0. Treatment continued for Days 1, 2, 3, and 4. Water samples were also taken at Day 2 and Day 5. FIG. 6 indicates that treating dental lines with Biocidal Complex caused a significant decrease in the number of organisms recovered from the effluent by day 2 and an even greater drop by day 5. Biocidal Complex was effective in reducing the number of organisms in the effluent of dental water lines contaminated with biofilms.

As seen in FIG. 6, the effects of the Biocidal Complex on a biofilm population established over a long period is less dramatic than with the model biofilms of FIGS. 4 and 5 where the establishment of the biofilm occurred for only five days. However, the results still show the effectiveness of the Biocidal Complex in treating the more mature, established biofilm.

EXAMPLE 4

Occasional Treatment With Complete Biocidal Complex

Experiments were performed to determine whether the continual use of complete Biocidal Complex was necessary to keep bacterial levels low or whether only an occasional inclusion of disinfectant might be sufficient. Glass beads and TYGON® tubing were contaminated and treated in 12 hour cycles as described in Examples 1 and 2 above. On day 0, the surfaces of the glass beads or TYGON® tubing were treated for 12 hours with 50 ml of Biocidal Complex containing 0.05% chlorhexidine (instead of thymol), 5 g mannitol peroxide, 0.03 g $NaHSO_4$, and an iron chip. For the next 5 days (days 1–5), the treatment was performed with 50 ml of an incomplete Biocidal Complex, i.e., without the disinfectant chlorhexidine. The surfaces were not treated on days 6, 7, 11 and 13. On day 8, the surfaces were treated with the Biocidal Complex prepared with 0.10% chlorhexidine, 5 g mannitol peroxide, 0.03 g $NaHSO_4$, and an iron chip. On days 9, 10, 12, and 14, the surfaces were again treated with the incomplete Biocidal Complex (without the chlorhexidine). Water samples were taken immediately prior to treatment (Day 0) and then at 24 hour intervals, following each treatment cycle. Microbial counts were monitored using standard water analysis procedures, as described in Mayo et al., 1999, and expressed as colony-forming units per milliliter of effluent (cfu/ml).

TABLE 3

Effect of occasional treatment with complete Biocidal Complex on biofilms

| Time (days) | Glass beads Control | Glass beads Treated | TYGON ® tubing Control | TYGON ® tubing Treated |
|---|---|---|---|---|
| 0 (+0.05% chlorhexidine) | 61,000,000 | 105,000,000 | 74,000 | 112,000 |
| 1 | 33,000,000 | 12,000 | 520,000 | 109,000 |
| 2 | 25,200,000 | 9,200 | 58,000 | 80 |
| 3 | 24,000,000 | 16,800 | 62,000 | 20 |
| 4 | 800,000 | 4,600 | 87,000 | 100 |
| 5 | 880,000 | 880 | 40,000 | 170 |
| 6[a] | | | | |
| 7[a] | | | | |
| 8 | 600,000 | 400 | 169,000 | 1 |
| (+0.10% chlorhexidine) | | | | |
| 9 | 760,000 | 2,200 | 59,000 | 600 |
| 10 | 1,670,000 | 3,040 | 21,000 | 440 |
| 11[a] | | | | |
| 12 | 560,000 | 420 | 63,000 | 1,770 |
| 13[a] | | | | |
| 14 | 440,000 | 30 | 3,000 | 20 |

[a]No treatment and no water sample taken.

The results as shown in Table 3 indicate that the disinfectant can be added periodically and still maintain a low bacterial count. However, for high quality water standards, e.g., for dental water lines, continual use of the complete Biocidal Complex may be necessary to keep bacterial counts below the standard.

EXAMPLE 5

Long Term Storage in Biocidal Complex

TYGON® tubing was contaminated by a five-day exposure to city water. Biofilm-contaminated TYGON® tubing was stored for 7 days with water (control), with complete Biocidal Complex (mannitol peroxide, $NaHSO_4$ and thymol) and an iron chip, or with a partial combination of mannitol peroxide and $NaHSO_4$ with an iron chip. The concentrations were as in part A of Example 2. The effluent from the tubing was sampled prior to beginning treatment on day 0 and after treatment was completed on day 7. Samples were analyzed as described above in Example 4, and results expressed as colony forming units per ml (cfu/ml).

TABLE 4

Effect of Biocidal Complex on long term storage in TYGON ® tubing

| Treatment | Day 0 | Day 7 |
|---|---|---|
| TYGON ® tubing-complete Biocidal Complex | | |
| Control (water only) | 78,000 | 83,000 |
| Treated (mannitol peroxide, $NaHSO_4$, thymol and iron chip) | 50,000 | 1,900 |
| TYGON ® tubing-partial Biocidal Complex | | |
| Control (water only) | 60,000 | 56,000 |
| Treated (mannitol peroxide, $NaHSO_4$, and iron chip) | 1,770 | 7,800 |

The bacterial count was significantly reduced by a partial complex (without the disinfectant) and by the complete complex during long term storage (for seven days). However, the largest reduction was with the complete Biocidal Complex, which included the disinfectant. This treatment reduced the number of organisms in the effluent from biofilm-contaminated TYGON® tubing from 50,000 to 1,900 cfu/ml after 7 days of storage. Thus continued use of Biocidal Complex decreased the number of bacteria and suppressed regrowth of bacterial populations.

EXAMPLE 6

Biocidal Activity Against Biofilms on Chicken Skin

To test the effectiveness of Biocidal Complex on other surfaces, a 5.7 $cm^2$ piece of chicken leg skin was placed in a holder made from a bottomless 50 ml centrifuge tube with a cap to support the skin test strip. Each skin sample was initially immersed in water. Then the skin was washed with 5 ml of 0.7% NaCl, and the surface swabbed to collect adherent bacteria. The bacteria were counted as described below. This value served as the control. The skin was then exposed to germicidal ultraviolet light for 5 min to sanitize the skin prior to inoculation. The sanitized skin was inoculated with 1 ml of a cell suspension containing 108 cfu/ml of either *Salmonella typhimurium* or *Escherichia coli* B and incubated for 30 min at 37° C. and 32° C., respectively. The inoculated skin samples were immersed in Biocidal Complex or in other combinations of ingredients at 20° C. for 10 min. The treated skin samples were then washed with 5 ml of 0.7% NaCl, and the surface swabbed to collect adherent bacteria. The cotton swabs from both the control and treated skin were vortex-mixed for 1 min in a 0.1% peptone solution (pH 7.2). Then 0.5 ml of peptone solution was plated on MacConkey agar (Difco Laboratory, Detroit, Michigan). The plates were incubated for 24 hr at either 37° C. or 32° C. before counting the colonies. Microbial counts were expressed as $cfu/cm^2$, based on a total skin sample area of 5.7 $cm^2$. An initial level of contamination before treatment with Biocidal Complex (or water) was assessed for each sample. A minimum inhibitory concentration (MIC) for any compound was determined as the concentration (as expressed in percentage) needed to reduce the final microbial count below 17.5 $cfu/cm^2$.

A. *Escherichia coli* Biofilm on Chicken Skin:

Initial contamination level of the inoculated skin after 30 min incubation time and immediately prior to treatment was 140,000 $cfu/cm^2$. Water-washed control skin had 15,800 $cfu/cm^2$.

TABLE 5

Concentrations of various combinations required to kill *Escherichia coli* on chicken skin (Minimum Inhibitory Concentration (MIC))

| Treatment | MIC (%) |
|---|---|
| Thymol* | >0.1 |
| $H_2O_2$ | 4.0 |
| $NaHSO_4$ | 2.0 |
| Thymol: $NaHSO_4$ | 0.02: 0.24 |
| $H_2O_2$: Thymol | 0.5: 0.08 |
| $H_2O_2$: $NaHSO_4$ | 0.5: 0.24 |
| $H_2O_2$: $NaHSO_4$: Thymol | 0.25: 0.12: 0.005 |
| Sodium Hypochlorite | 1.0 |

*Requires a saturated solution which is greater than 0.1%.

As seen in Table 5, the lowest MIC was for the complete Biocidal Complex. The concentrations required to achieve comparable results were higher when fewer components were used.

B. *Salmonella Typhimurium* Biofilm on Chicken Skin:

Contamination level of the inoculated skin after 30 min incubation time and immediately before treatment was 3,500,000 cfu/cm$^2$. The water-washed control skin ha 1,750 cfu/cm$^2$.

TABLE 6

Concentrations of various combinations required to kill *Salmonella typhimurium* on chicken skin (Minimum Inhibitory Concentration MIC))

| Treatment | MIC (%) |
|---|---|
| Thymol* | >0.1 |
| H$_2$O$_2$ | 7.0 |
| NaHSO$_4$ | 5.0 |
| Thymol: NaHSO$_4$ | 0.04: 0.48 |
| H$_2$O$_2$: Thymol | 0.35: 0.04 |
| H$_2$O$_2$: NaHSO$_4$ | 0.35: 0.48 |
| H$_2$O$_2$: NaHSO$_4$: Thymol | 0.25: 0.24: 0.01 |
| Sodium Hypochlorite | 1.0 |

*Requires a saturated solution which is greater than 0.1%.

EXAMPLE 7

Biocidal Activity in Broth Cultures

Nutrient broth was mixed with the complete Biocidal Complex or with combinations of ingredients, and then serially diluted two-fold in stages. Various combinations of biocidal ingredients and broth were inoculated with 0.1 ml of either *Salmonella typhimurium* or *Escherichia coli* B to give a microbial count of about 107 cfu/ml. Inoculated broth was then incubated for 24 hours at 37° C. for *S. typhimurium*, or at 32° C. for *E. coli*. The MIC was determined as the minimum concentration of the ingredient that prevented detectable microbial growth after 24 hr.

TABLE 7

Concentrations of various combinations required to kill bacteria in broth culture (Minimum Inhibitory Concentration MIC))

| Chemical | MIC (%) |
|---|---|
| A. *Escherichia coli* in broth culture | |
| Thymol* | 0.02 |
| H$_2$O$_2$ | 0.006 |
| NaHSO$_4$ | 0.19 |
| Thymol: NaHSO$_4$ | 0.002: 0.002 |
| H$_2$O$_2$: Thymol | 0.003: 0.015 |
| H$_2$O$_2$: NaHSO$_4$ | 0.006: 0.019 |
| H$_2$O$_2$: NaHSO$_4$: Thymol | 0.003: 0.094: 0.01 |
| Sodium hypochlorite | 0.013 |
| B. *Salmonella typhimurium* in broth culture | |
| Thymol* | 0.04 |
| H$_2$O$_2$ | 0.012 |
| NaHSO$_4$ | 0.019 |
| Thymol: NaHSO$_4$ | 0.004: 0.004 |
| H$_2$O$_2$: Thymol | 0.006: 0.02 |
| H$_2$O$_2$: NaHSO$_4$ | 0.006: 0.094 |
| H$_2$O$_2$: NaHSO$_4$: Thymol | 0.006: 0.047: 0.013 |
| Sodium hypochlorite | 0.025 |

These experiments demonstrated that Biocidal Complex and its various ingredients can exert biocidal activity against bacterial growth in a liquid culture. However, under these conditions the combination of ingredients did not show the same synergistic effect that was seen when the complex was used to kill bacteria on surfaces.

EXAMPLE 8

Biocidal Activity on Biofilm-contaminated Surfaces Used in Food Processing

Stainless steel chips (1 cm×1 cm) were washed with 1 N NaOH for 24 hr to clean the surface. Each chip was then washed with distilled water and sterilized at 121° C. for 15 min. The sterilized chips were inoculated with 1 ml of a cell suspension of *S. typhimurium* and incubated at 37° C. for 30 min. Samples were washed with 5 ml of 0.7% NaCl solution to remove unattached cells and then immersed either in Biocidal Complex (a 0.06% peroxide solution containing a 10:1 ratio of peroxide to NaHSO$_4$ and 0.004% thymol) or in bleach (25 ppm of NaOCl). Samples were kept at either 4° C. or at 37° C. Samples were collected at various intervals up to 30 min. Each sample was drained and transferred to a 10 ml test tube containing 5 ml of 0.1% peptone solution (pH 7.2) and 0.5 g of glass beads. The tubes were vortex-mixed for 1 min. Then a 0.5 ml sample of peptone solution was plated on MacConkey agar, and the plates incubated at 37° C. for 24 hr. A dramatic reduction in the levels of biofilm organisms recovered from chips treated with Biocidal Complex was found.

Figure 7A:
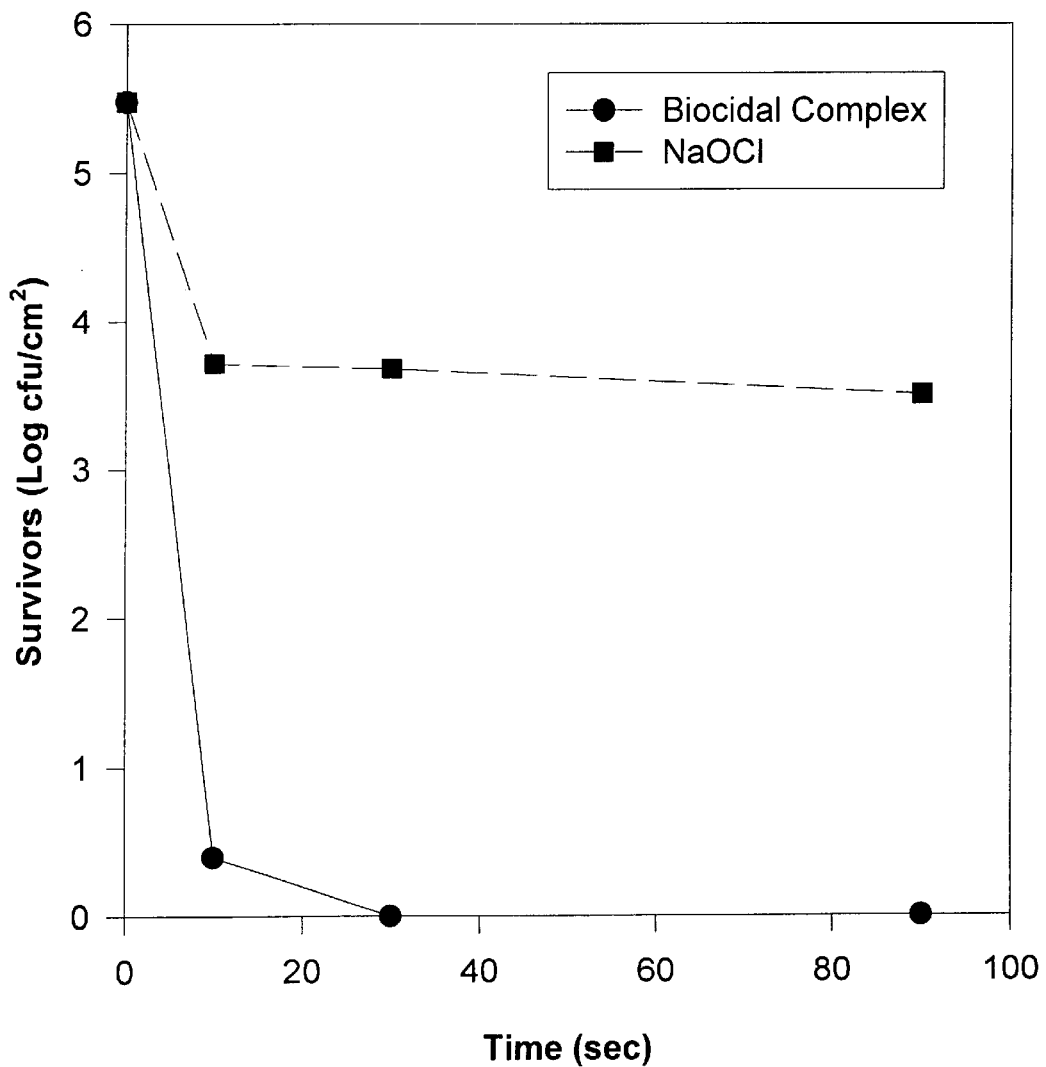
FIG. 7a illustrates the timed decrease in bacterial concentration on biofilm-contaminated stainless steel after treatment at 37° C. with either bleach or Biocidal Complex, comprising hydrogen peroxide, sodium bisulfate, and thymol.
Figure 7B:
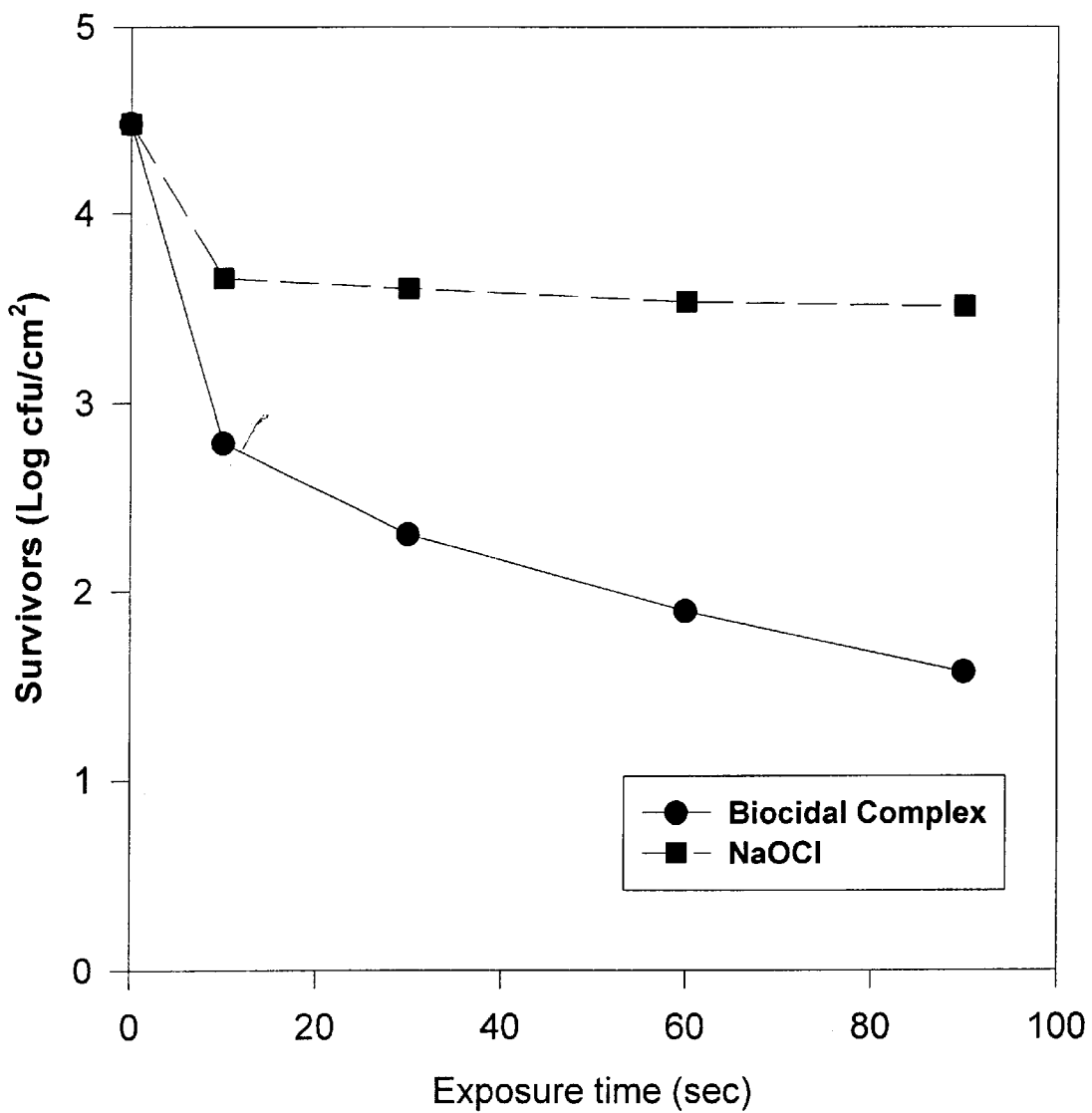
FIG. 7b illustrates the timed decrease in bacterial concentration on biofilm-contaminated stainless steel after treatment at 4° C. with either bleach or Biocidal Complex, comprising hydrogen peroxide, sodium bisulfate, and thymol.

FIGS. 7a and 7b illustrate the kill response time for bacteria after treatment with bleach and Biocidal Complex at 37° C. and 4° C., respectively. The Biocidal Complex decreased the number of bacteria to almost zero within 30 sec and was more effective than the bleach at both temperatures.

EXAMPLE 9

Spraying Biocidal Complex on Surfaces With Adhered Cells

A. Chicken Skin.

Chicken skin was prepared as described in Example 6. Samples were washed with 5 ml of a 0.7% NaCl solution to remove unattached cells. Stock solutions of Biocidal Complex (comprising 2.5% H$_2$O$_2$, 0.25% NaHSO$_4$, and 0.1% thymol) or of bleach (4% NaOCl) were diluted. Five ml of various concentrations was sprayed on the test skin surface (with an approximate area of 5.7 cm$^2$) with continuous drainage. After 1 min, the sprayed skins were swabbed for microbial collection. The swabs were treated and analyzed for bacterial growth as in Example 8. Both Biocidal Complex and bleach caused significant reductions in the levels of biofilm organisms with dilute solutions. (Data not shown) Bleach caused the bacterial count to fall to zero at a dilution of 1:200 of the stock solution. A 1:250 dilution of Biocidal Complex caused a similar decrease in bacteria. These results indicated that Biocidal Complex is as effective as bleach in removing bacteria from organic material.

B. Stainless Steel Chips.

Chips of stainless steel were prepared as described in Example 8. Samples were washed with 5 ml of 0.7% NaCl solution to remove non-adherent cells. Ten ml of various dilutions of stock Biocidal Complex, prepared as described in part A of this example, or of bleach was sprayed on the stainless steel chips with continual drainage. After 1 min, each stainless steel chip was transferred to a 10 ml test tube containing 5 ml of 0. 1% peptone solution (pH 7.2) and 0.5 g glass beads. The test tubes were vortex-mixed for 1 min. Then a 0.5 ml sample of the peptone solution was plated on MacConkey agar, and the plates incubated at 37° C. for 24 hr. The two treatments were effective at very dilute solutions. (Data not shown.) The bacterial count fell to zero at dilutions of 1:5000 and 1:20,000 of the 4% bleach stock and of the Biocidal Complex, respectively. The Biocidal Complex is very effective in removing bacteria from inanimate material.

The term "effective amount" of a biocidal complex as used in the specification and the claims refers to an amount of biocidal complex that is sufficient to reduce the effluent or surface microbial count to the level recommended by the industry standard applicable to a given use. An "effective amount" of a biocidal complex therefore includes, for example, an amount of biocidal complex sufficient to reduce the bacterial count in effluent from dental lines to a level recommended by the American Dental Association. The time of exposure, method of application, and concentration of components will vary with each use. A person of ordinary skill in the art, given the teachings of the present specification, may readily determine suitable treatment regimes for particular applications.

The complete disclosures of all references cited in this specification are hereby incorporated by reference. Also incorporated by reference is the complete disclosure of the following abstract: D. W. Kim et al., "Effect of a novel biocide as an alternative to chlorine treatment for *Salmonella typhimurium* and *Escherichia coli*," 99$^{th}$ American Society for Microbiology General Meeting, Jun. 1, 1999, Chicago, Ill., Abstract No. P-57 (1999). In the event of an otherwise irreconcilable conflict, however, the present specification shall control.

We claim:

1. A biocidal complex active against biofilms, said biocidal complex comprising a free-radical generator, an acid sulfate, and a disinfectant, wherein the free radical generator is selected from the group consisting of hydrogen peroxide, mannitol peroxide, sodium peroxide, and barium peroxide; peroxyacids, and superoxides.

2. A biocidal complex as recited in claim 1, additionally comprising a catalyst to promote the release of free radicals from the fee-radical generator.

3. A biocidal complex as recited in claim 2, wherein said catalyst is selected from the group consisting of iron, copper, cobalt, silver, gold, chromium, zinc, and nickel.

4. A biocidal complex as recited in claim 2, wherein said catalyst comprises iron.

5. A biocidal complex as recited in claim 1, wherein said free-radical generator comprises hydrogen peroxide.

6. A biocidal complex as recited in claim 1, wherein said free-radical generator comprises mannitol peroxide.

7. A biocidal complex as recited in claim 1, wherein said acid sulfate is selected from the group consisting of sodium bisulfate or potassium bisulfate.

8. A biocidal complex as recited in claim 1, wherein said acid sulfate comprises sodium bisulfate.

9. A biocidal complex as recited in claim 1, wherein said disinfectant comprises thymol.

10. A biocidal complex as recited in claim 1, wherein said disinfectant comprises chlorhexidine.

11. A biocidal complex as recited in claim 1, wherein said complex comprises:
   (a) between about 0.001 parts and about 20 parts hydrogen peroxide by weight;
   (b) between about 0.0001 parts and about 2 parts sodium bisulfate by weight; and
   (c) between about 0.05 parts and about 0.1 parts thymol by weight.

12. A biocidal complex as recited in claim 11, wherein said complex comprises about 2.5 parts hydrogen peroxide.

13. A biocidal complex as recited in claim 11, wherein said complex comprises about 0.06 parts sodium bisulfate.

14. A biocidal complex as recited in claim 11, wherein said complex comprises about 0.1 parts thymol.

15. A two-component, stable system for preparing a biocidal complex, said system comprising Part A and Part B; wherein Part A and Part B are maintained in separate containers prior to use; wherein Part A comprises a free-radical generator; and wherein Part B comprises an acid sulfate and a disinfectant; and wherein the free radical generator is selected from the group consisting of hydrogen peroxide, mannitol peroxide, sodium peroxide, and barium peroxide; peroxyacids, and superoxides.

16. A method for removing at least part of a biofilm from a surface, said method comprising applying to the surface an effective amount of a biocidal complex comprising a free-radical generator, an acid sulfate, and a disinfectant, wherein the free radical generator is selected from the group consisting of hydrogen peroxide, mannitol peroxide, sodium peroxide, and barium peroxide; peroxyacids, and superoxides.

17. A method as recited in claim 16, additionally comprising the step of reacting the complex over a catalyst to promote the release of free radicals from the free-radical generator.

18. A method as recited in claim 16, wherein said free-radical generator comprises hydrogen peroxide.

19. A method as recited in claim 16, wherein said free-radical generator comprises mannitol peroxide.

20. A method as recited in claim 16, wherein said catalyst is selected from the group consisting of iron, copper, cobalt, silver, gold, chromium, zinc, and nickel.

21. A method as recited in claim 16, wherein said catalyst comprises iron.

22. A method as recited in claim 16, wherein said acid sulfate is selected from the group consisting of sodium bisulfate or potassium bisulfate.

23. A method as recited in claim 16, wherein said acid sulfate comprises sodium bisulfate.

24. A method as recited in claim 16, wherein said disinfectant comprises thymol.

25. A method as recited in claim 16, wherein said disinfectant comprises chlorhexidine.

26. A method as recited in claim 16, wherein said biofilm is on the surface of organic material.

27. A method as recited in claim 16, wherein said biofilm is on the surface of inorganic material.

* * * * *